(12) United States Patent
Rubin et al.

(10) Patent No.: US 10,029,089 B2
(45) Date of Patent: Jul. 24, 2018

(54) COMPOSITIONS AND METHODS FOR ENHANCING THE BIOLOGICAL RESPONSE TO CHEMICAL AGENTS AND PHYSICAL STIMULI

(75) Inventors: Clinton Rubin, Port Jefferson, NY (US); Janet Rubin, Chapel Hill, NC (US)

(73) Assignees: RESEARCH FOUNDATION FOR THE STATE UNIVERSITY OF NEW YORK, THE, Albany, NY (US); NORTH CAROLINA AT CHAPEL HILL, UNIVERSITY OF, Chapel Hill, NC (US)

( * ) Notice: Subject to any disclaimer, the term of this patent is extended or adjusted under 35 U.S.C. 154(b) by 936 days.

(21) Appl. No.: 13/879,551

(22) PCT Filed: Oct. 14, 2011

(86) PCT No.: PCT/US2011/056289
§ 371 (c)(1),
(2), (4) Date: Jul. 8, 2013

(87) PCT Pub. No.: WO2012/051495
PCT Pub. Date: Apr. 19, 2012

(65) Prior Publication Data
US 2013/0288260 A1    Oct. 31, 2013

Related U.S. Application Data

(60) Provisional application No. 61/393,812, filed on Oct. 15, 2010.

(51) Int. Cl.
*A61N 1/05* (2006.01)
*A61N 1/36* (2006.01)
(Continued)

(52) U.S. Cl.
CPC .......... *A61N 1/05* (2013.01); *A61M 5/00* (2013.01); *A61N 1/36* (2013.01); *A61N 2/02* (2013.01);
(Continued)

(58) Field of Classification Search
CPC .......... C12N 5/0663; C12N 2527/00; A61H 23/0236; A61H 2201/165
(Continued)

(56) References Cited

U.S. PATENT DOCUMENTS 3,658,051 A * 4/1972 MacLean ............. A61N 2/02
                                                                324/263
4,529,401 A    7/1985 Leslie et al.
(Continued)

FOREIGN PATENT DOCUMENTS

WO    2007137123 A2    11/2007
WO    WO2009/108953    *   9/2009    ........... A61N 2/00

OTHER PUBLICATIONS

Conversion Between Displacement, Velocity, and Acceleration . 6 pages, printed from internett Aug. 22, 2016.*
(Continued)

*Primary Examiner* — Samuel Gilbert
(74) *Attorney, Agent, or Firm* — Carter, DeLuca, Farrell & Schmidt, LLP

(57) ABSTRACT

The present invention relates to compositions and methods configured to deliver a stimulus (e.g., a therapeutic agent or a therapeutically beneficial signal) to a cell, tissue, organ, or organism. The stimulus is applied at least twice, and the first and second applications are separated by a rest period in which no further stimulus is actively applied. The rest period is of a duration (e.g., about 1-6 hours) sufficient to provoke an enhanced response to the second stimulus.

13 Claims, 2 Drawing Sheets

Sine wave. A sine wave burst, of duration t, of a given physical modality (e.g., mechanical) is separated by a rest period (T), before a second burst (t') of physical signal is delivered.

Square wave with refractory period.

Chirp signal with refractory period

Sawtooth wave with refractory period.

Stochastic (chaotic) wave with refractory period.

Sin wave with refractory period before a sawtooth wave is introduced

Sin wave burst with refractory period followed by multiple burst/refractory period stimuli.

(51) Int. Cl.
  *A61N 2/02* (2006.01)
  *A61M 5/00* (2006.01)
  *C12N 13/00* (2006.01)
  *A61M 31/00* (2006.01)
  *A61N 2/00* (2006.01)
  *A61N 5/06* (2006.01)
  *A61N 1/32* (2006.01)

(52) U.S. Cl.
  CPC ........... *C12N 13/00* (2013.01); *A61M 31/002* (2013.01); *A61N 1/326* (2013.01); *A61N 2/00* (2013.01); *A61N 5/062* (2013.01)

(58) Field of Classification Search
  USPC .......................................................... 128/898
  See application file for complete search history.

(56) References Cited

U.S. PATENT DOCUMENTS

| | | | |
|---|---|---|---|
| 4,858,598 | A | 8/1989 | Halpern |
| 4,858,599 | A | 8/1989 | Halpern |
| 4,967,736 | A | 11/1990 | Spitzer |
| 5,069,668 | A | 12/1991 | Boydman |
| 5,188,095 | A | 2/1993 | Healy |
| 5,273,028 | A | 12/1993 | McLeod et al. |
| 5,376,065 | A | 12/1994 | McLeod et al. |
| 5,914,345 | A | 6/1999 | Slepian et al. |
| 6,080,127 | A | 6/2000 | Li et al. |
| 6,190,336 | B1 | 2/2001 | Duarte et al. |
| 6,387,116 | B1 | 5/2002 | McKenzie et al. |
| 6,391,026 | B1 | 5/2002 | Hung et al. |
| 6,561,991 | B2 | 5/2003 | McLeod et al. |
| 6,607,497 | B2 | 8/2003 | McLeod et al. |
| 6,610,323 | B1 | 8/2003 | Lundberg et al. |
| 6,876,883 | B2 | 4/2005 | Hurtado |
| 7,483,747 | B2 | 1/2009 | Gliner et al. |
| 7,575,574 | B2 | 8/2009 | Shachar |
| 2004/0033533 | A1 | 2/2004 | Yano et al. |
| 2004/0259789 | A1 | 12/2004 | Chada et al. |
| 2004/0260356 | A1 | 12/2004 | Kara et al. |
| 2005/0019765 | A1 | 1/2005 | Wellington et al. |
| 2005/0084487 | A1 | 4/2005 | Paszty |
| 2005/0090457 | A1 | 4/2005 | Schoenmakers et al. |
| 2005/0153437 | A1 | 7/2005 | Kishida et al. |
| 2006/0047230 | A1 | 3/2006 | Talish |
| 2006/0058243 | A1 | 3/2006 | Chen et al. |
| 2007/0299539 | A1 | 12/2007 | Othman et al. |
| 2008/0195007 | A1* | 8/2008 | Podrazhansky .... A61H 23/0236 601/47 |
| 2009/0177147 | A1 | 9/2009 | Blomquist et al. |
| 2010/0028968 | A1 | 2/2010 | Rubin et al. |
| 2011/0070206 | A1* | 3/2011 | Rubin .................. C12N 5/0663 424/93.7 |

OTHER PUBLICATIONS

Li, et al., "Oscillatory Fluid Flow Affects Human Marrow Stromal Cell Proliferation and Differentiation." Journal of Orthopaedic Research, 2004; 22:1283-1289.
Luu et al., "Mech. Inf. of Mesenchymal Stem Cell Diff. as a Means to Enhance Bone Form.: Are Osteoblasts the Only Way to a Better Skeleton?", ORS 2008, printed Sep. 5, 2007, 3pgs.
Supplementary European Search Report dated Jan. 7, 2013 for EP 07 78 3881.
Park et al., "Differential Effects of Equiaxial and Uniaxial Strain on Mesenchymal Stem Cells", Biotechnology and Bioengineering, vol. 88, No. 3, pp. 359-368 (2004).
Wang et al., "An Introductory Review of Cell Mechanobiology", Biomechanics and Modeling in Mechanobiology, vol. 5, No. 1, pp. 1-16 (2006).
Cara et al., Type 2 Diabetes and the Metabolic Syndrome in Children and Adolescents, Current Diabetes Reports, 6:241-250 (2006).
Adams et al., Overweight, Obesity, and Mortality in a Large Prosp. Cohort of Persons, New England J. of Med., vol. 355, No. 8, pp. 763-778 (2006).
Petersen et al., Etiology of Insulin Resistance, Am. J. Med., 119:S10-S16 (2006).
Unger, Minireview: Weapons of Lean Body Mass Destruction, Endocrinology, 144(12):5159-65 (2003).
Fritton et al., Whole-Body Vibration in the Skeleton, Annals of Biomedical Engineering, vol. 25, pp. 831-839 (1997).
Folch et al., A Simple Method for the Isolation and Purification of Total Lipids, J. Biol. Chem, 226:497-509 (1957).
Watts et al., Adipose Tissue Compartments and the Kinetics of Very-Low-Density Lipoprotein, Metabolism, vol. 51, No. 9:1206-1210 (2002).
Rubin et al., Molecular Pathways Mediating Mechanical Signaling in Bone, GENE, Sec. Functional Genomics, 367:1-16 (2006).
Skerry et al., Loading-Related Reorientation of Bone Proteoglycan in Vivo, Journal of Orthopaedic Res., 6:547-551 (1988).
Rubin et al., Adipogenesis is Inhibited by Brief, Daily Exp. to High-Frequency, Extremely Low-Mag. Mech. Signals, PNAS, vol. 104, No. 45, pp. 17879-17884 (2007).
Dehghan et al., Childhood Obesity, Prevalence and Prevention, Nutrition Journal, 4:24 (2005).
Stumvoll et al., Type 2 Diabetes: Principles of Pathogenesis and Therapy, Lancet, 365:1333-46 (2005).
Frank et al., Effects of Exercise on Metabolic Risk Variables in Overweight Postmenopausal Women, Obesity Res., vol. 13, No. 3, pp. 615-625 (2005).
Colombo et al., Prevention of Hyperclycemia in Zucker Diabetic Fatty Rats, Metabolism Clinical and Exp., 54:1571-81 (2005).
Perusse et al., The Human Obesity Gene Map, Obesity Res., vol. 13, No. 3, pp. 381-490 (2005).
Bacabac, et al., Bone Cell Responses to High-Frequency Vibration Stress: Does the Nucleus Oscillate Within the Cytoplasm? The FASEB Journal, May 2006, 20: 858-864.
Huang, et al., "Differentation from Embryonic Stem Cells to Vascular Wall Cells under In Vitro Pulsatile Flow Loading." J. Artif. Organs, 2005, 8:110-118, pub on Aug. 1, 2005.
Altman, et al., "Cell Differentiation by Mechanica Stress", The FASEB J. [online], Exp. article pub online Dec. 28, 2001 [ret. Jan. 18, 2012], ret from the Internet: www.fasebj.org.
Hamilton, et al., "Charact. of the Resp. of Bone Marrow-Derived Progenitor Cells to Cyclic Strain: Impl. for Vascular Tissue-Eng. Apps.", Tissue Eng. 2004, 10(3/4):361-369.
Brown, SA et al. Osteoporosis: An under-appreciated complication of diabetes. Clinical Diabetes. 2004. 22(1 ): 10-20.
European Office Action for EP 07 783 881.1 dated Mar. 2, 2015.
David, V et al. Mechanical loading down-regulates peroxisome proliferator-activated receptor gamma in bone marrow stromal cells and favors osteoblastogenesis at the expense of adipogenesis. Endocrinology. 2007. 148(5): 2553-2562. Published online on Feb. 22, 2007.
Duarte, VMG et al. Osteopenia: a bone disorder associated with diabetes mellitus. J. Bone Miner. Metab. Jan. 2005. 23: 58-68.
Alberti, KGMM et al. Definition, diagnosis and classification of diabetes mellitus and its complications part 1: diagnosis and classification of diabetes mellitus provisional report of a WHO consultation. Diabetic Medicine. 1998. 15: 539-553.
Canadian Examination Report for Canadian Patent No. 2,717,083, dated Mar. 13, 2015.
European Examination Report for EP 09 714 997.5 dated Mar. 5, 2015.
Australian Patent Examination Report No. 1 dated Apr. 17, 2013 for AU 2009219016.
Australian Patent Examination Report No. 2 dated Jun. 11, 2014 for AU 2009219016.
Rubin, C et al. Quantity and quality of trabecular bone in the femur are enhanced by a strongly anabolic, noninvasive mechanical intervention. Journal of Bone and Mineral Research. 2002. 17(2): 349-357.
Sutherland, FWH et al. From stem cells to viable autologous semilunar heart valve. Circulation. 2005. 111: 2783-2791.

(56) References Cited

OTHER PUBLICATIONS

McGarry, James G. et al., "A comparison of strain and fluid shear stress in stimulating bone cell responses—a computational and experimental study", pp. 1-22, The FASEB Journal express article 10.1096/fj. Published online Dec. 29, 2004, © 2004 FASEB.
Owan, I. et al., "Mechanotransduction in bone: osteoblasts are more responsive to fluid forces than mechanical strain" American Journal of Physiology—Cell Physiology, Abstract, ©1997, The American Physiological Society. 1 Page.
European Search Report for EP 09 71 4997 dated Jun. 17, 2013.
Saha et al., "Inhibition of Human Embryonic Stem Cell Differentiation by Mechanical Strain", Journal of Cellular Physiology, 206:126-137 (2006).
Rosenberg et al., "Experimental Model for Stimulation of Cultured Human Osteoblast-Like Cells by High Frequency Vibration", Cytotechnology, 39:125-130 (2002).
Judex et al., "Low-Mag. Mech. Signals that Stimulate Bone Form. in the Ovariectomized Rat are Dep. on App. Freq. but not on Strain Mag.", J. of Biomech., 40:1333-1339 (2007).
Xie et al., "Low-Level Mechanical Vibrations Can Influence Bone Resorption and Bone Formation in the Growing Skeleton", Bone 39: 1059-1066 (2006).

\* cited by examiner

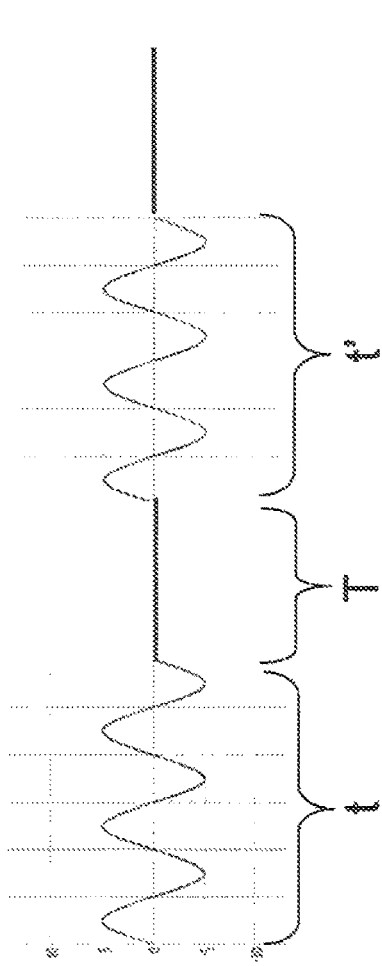
Sine wave. A sine wave burst, of duration t, of a given physical modality (e.g., mechanical) is separated by a rest period (T), before a second burst (t') of physical signal is delivered.
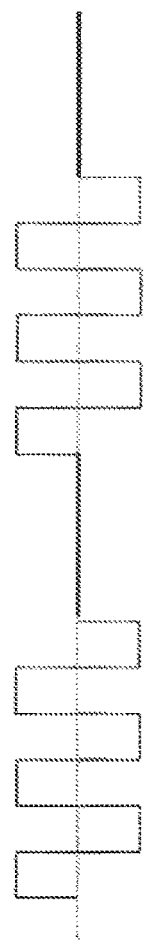
Square wave with refractory period.
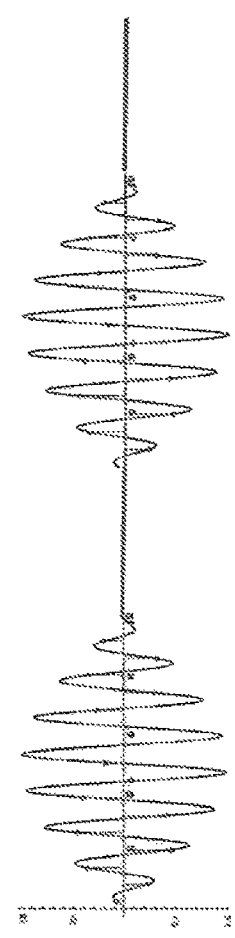
Chirp signal with refractory period

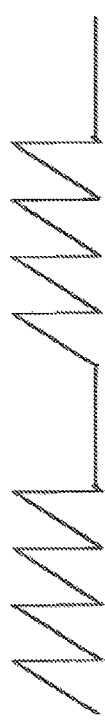
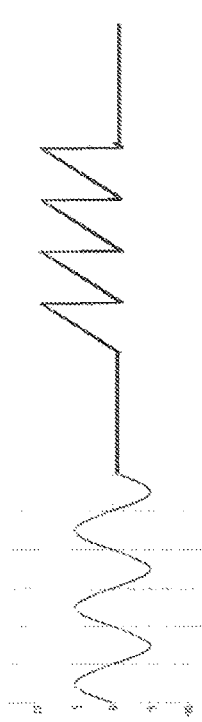
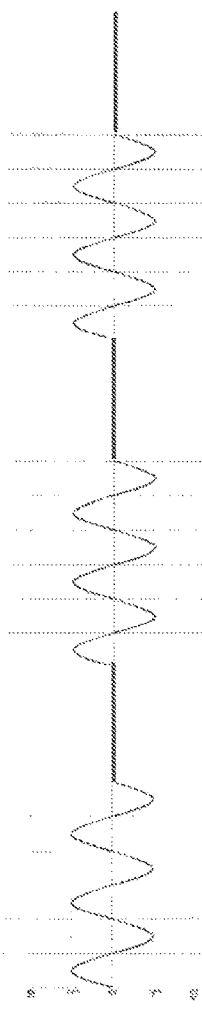

COMPOSITIONS AND METHODS FOR ENHANCING THE BIOLOGICAL RESPONSE TO CHEMICAL AGENTS AND PHYSICAL STIMULI

CROSS-REFERENCE TO RELATED APPLICATIONS

This application claims the benefit of the thing date of U.S. Provisional Application No. 61/393,812, which was filed Oct. 15, 2010. The entire content of U.S. Provisional Application No. 61/393,812 is hereby incorporated by reference in the present application in its entire.

STATEMENT REGARDING FEDERALLY FUNDED RESEARCH

This invention was made with government support awarded by the National Institutes of Health under Grant No. AR43498. The U.S. government has certain rights in this invention.

SEQUENCE LISTING

The present application contains a Sequence Listing that has been submitted in ASCII format via EFS-Web and is hereby incorporated by reference into the present specification in its entirety.

FIELD OF THE INVENTION

The present invention relates to compositions and methods for impacting a wide variety of physiological conditions and, more particularly, to compositions or devices that are configured to deliver a chemical agent (whether prophylactic or therapeutic, such as a nutriceutical or pharmaceutical agent) or a physical stimulus (e.g., a high frequency, low magnitude mechanical stimulus) to a cell, tissue, organ, or organism according to a schedule in which periods of rest are interposed between applications of the agent or signal.

SUMMARY

The present invention is based, in part, on our studies of refractory or rest periods in biological systems. Accordingly, the compositions and methods of the present invention feature the application of a stimulus to a biological cell, tissue, organ, or organism over time, with periods of rest interposed between the stimuli. While the invention is not so limited, our studies indicate that a second stimulus is more effective when there is a period of rest between the application of a first stimulus and the application of a second stimulus and, further, that efficacy may increase even further when subsequent stimuli are applied after rest. For example, rather than exposing a patient to an ultrasound treatment once a day for 20 minutes (as with the EXOGEN SAFHS ultrasound treatment of fractures; see also U.S. Pat. No. 7,789,841), one can augment the response by administering two 10-minute periods of ultrasonic treatment separated by a three hour period of rest (i.e., no application of ultrasonic waves). We expect that three applications (e.g., three 10- or 20-minute periods of applying the stimulus), each separated by about three hours of rest, will further amplify the response. Likewise, rather than delivering pulsed electromagnetic fields once a day for eight hours (as with EBI PEMF Coils for delayed/non-union; see also U.S. Pat. No. 7,744,869), splitting this stimulus into several (e.g., 2 or 3) shorter bouts of the same or lesser intensity would enhance responsiveness and efficacy. As described further below, devices can be optionally programmed or designed to deliver and then withhold delivery of the stimulus as described herein (e.g., with refractory or rest periods occurring for about one to six hours). While the invention is not so limited, we believe the rest periods enable or promote responsiveness to a signal. Our work to date further indicates that imposing refractory or rest periods can actually amplify the expected response. For example, administering a stimulus three times a day, with intervening rest periods (rather than once a day) may produce up to an eight-fold higher response. The amount of a stimulus, in total (e.g., the amount provided to a cell, tissue, organ, or organism per day), can be more less, or about the same as the amount of the stimulus currently prescribed. For example, where a patient is typically prescribed a chemical agent at a dosage of 100 mg/day, the patient may receive, according to the present methods, about 50 mg of the agent at a first point in time and about 50 mg of the agent at a second point in time (i.e., about one to six hours later). In other instances, the response may be just as effective, or even more effective, if the patient receives less of the agent per day (e.g., 50 mg in divided doses per day). As we believe the refractory or rest period can promote responsiveness to a signal, our invention encompasses dosing patterns in which the amount of the stimulus is not equal in all applications. For example, about a third of the total stimulus may be given, at a first point in time and the remaining two-thirds may be given at the second point in time. With three applications, one may similarly provide increasingly greater doses over time.

Where the device can reasonably comfortably remain in close proximity to die patient (e.g., where the device is a transdermal patch containing a chemical agent), the methods can be carried out with minimal inconvenience as well as with enhanced responsiveness and efficacy. The same is true where the stimulus is supplied in a form other than a physical signal. For example, the same is true where the stimulus is a pharmaceutical agent rather than a physical stimulus. Thus, the present compositions and methods are broadly applicable and can be more effective than current regimes.

The details of one or more embodiments of the invention are set forth in the description below, the drawing, and the claims. Other features, objects, and advantages of the invention will be apparent from the description, the drawing, and the claims.

BRIEF DESCRIPTION OF THE DRAWING

FIG. 1 is a line drawing illustrating, by wave form analogy, examples of the patterning that can be employed in the periodic treatment methods described herein. The square wave illustrates embodiments in which a stimulus is applied abruptly, sustained at a given magnitude and then stopped abruptly prior to an essentially stimulus-free period. The other wave forms illustrate embodiments in which the stimulus is applied and stopped in other manners For example, the application of the stimulus can also be, as shown, akin to a sine wave, "chirp", sawtooth wave, or stochastic (chaotic). The inclusion of two types of waves in one line (representing one treatment regime) emphasizes that the stimuli described herein can be administered in any combination of the various forms of application (e.g., the stimuli can be administered abruptly and in a graded manner in the same treatment regime). The last line form illustrates that stimuli can be administered more than twice within a given treatment session.

DETAILED DESCRIPTION

The present invention features compositions (e.g., medical devices and pharmaceutical formulations) and methods for applying a stimulus to a target (e.g., a cell, tissue, organ, or organism) according to a particular regimen. The stimulus can take many forms, and stimuli useful in the present invention include not only chemical agents, such as conventional small organic pharmaceuticals and biotherapeutics, but also physical stimuli delivered by an energy source. The chemical agent can be, for example, a nucleic acid (e.g., a nucleic acid that mediates RNAi), peptides (e.g., insulin), and therapeutic immunoglobulins. The physical stimuli can be light energy (e.g., infrared, visible, or ultraviolet light), thermal energy (in the form of heat or cold), an electric current (e.g., capacitively coupled), or an electromagnetic field (e.g., induced field), a magnetic field, a sound wave or ultrasound wave, high or low magnitude mechanical signals (e.g., delivered by vibration) and/or radiation. The compositions and methods are configured such that the stimulus is delivered at two or more distinct points in time, the initiation of the first and second deliveries being separated by a particular and defined period of rest during which little or no stimulus is applied to the target. The periodic delivery, as described thither herein, achieves a better outcome than if the stimulus was delivered just once in the same period of time. For example, instead of applying an ultrasound treatnein once a day for three minutes (e.g., as an anti-angiogenic treatment in cancer therapy), one would instead apply the ultrasound twice; a first application for 1.5 minutes would be followed by a period of rest (e.g. a one to six hour period of rest from the stimulus) and then a second application for 1.5 minutes. The compositions and methods can be applied to, and are expected to benefit subjects in a great variety of circumstances. We believe that essentially any treatment can be improved by a delivery paradigm according to the present regimen.

In one aspect, the invention features a medical device configured to deliver a chemical agent or a physical stimulus to a cell, tissue, organ, or organism, wherein the agent or the stimulus is physiologically acceptable and the device comprises: a compartment containing the chemical agent or a means for delivering the physical stimulus to the cell, tissue, organ, or organism; and a mechanism that regulates the release of the agent or the delivery of the stimulus from the device, wherein the mechanism allows a first release for about one second to about one hour, prohibits release for at least or about the next 1-6 hours (e.g., about the next 1, 2, or 3 hours), and then allows a second release for about one second to about one hour. Throughout the description of the invention, it is to be understood that the stated ranges encompass all intervening values. For example, the range of about 1-6 hours encompasses 1.5 hours, 2 hours, 2 hours and 15 minutes, 3.5 hours, and so forth). "About" indicates variability within about 10%. The chemical agent or physical stimulus is "physiologically acceptable" in that it is non-toxic and/or does not injure the subject to an unacceptable extent.

In a device of the invention, the targeted cell, tissue, or organ can be a cell, tissue, or organ in vivo. The targeted cell, tissue, organ, or organism can also be a cell, tissue, organ, or organism maintained in cell culture. For example, the cell can be a bacterial, yeast, or mammalian cell. The tissue can be a mammalian tissue explant, and the organism can be a mammal (e.g., a human, non-human primate, canine, feline, bovine, porcine, or equine mammal). As noted, the present devices can be configured to be wholly confined within an organism (e.g., a mammalian subject). Where the device is configured to deliver a chemical agent, the device can be an ingestible tablet or capsule or an implantable pump, wherein the tablet, capsule, or pump contains the chemical agent. To deliver a chemical agent or physical stimulus in a tissue culture setting, the device can be free standing and self-contained or it can be associated with another device. For example, the device can be associated with a piece of tissue culture ware, such as a tissue culture dish or plate, a flask, a rotating platform, the floor of a tissue culture hood, or an incubator.

As noted, the present devices can be configured to deliver a physical stimulus to the subject, and that stimulus can be generated by an electrical current, a magnetic field, a sound wave, thermal energy, or light energy. In some embodiments, the physical stimulus is a high frequency, low magnitude mechanical stimulus. Such devices can be configured to be wholly confined within an organism (e.g., a mammalian subject). In other embodiments, the present devices are free-standing (e.g., a platform). In other embodiments, the present devices are integral to another device (e.g., an orthopedic device, a dental implant, a stent, an indwelling catheter, a feeding tube, a tracheostomy tube, an intubation tube, or a pacemaker).

The mechanism controlling the application of the stimulus (whether chemical or physical) can allow release and prohibit release on a regularly or irregularly repeating cycle. For example, the intervals between the administration or application of a stimulus can vary in length (e.g., they can become progressively longer (e.g., 10%, 50%, 100% or 200% longer at each successive interval), in some embodiments, the mechanism allowing release of the physical agent or chemical stimulus will allow release in periods that last for about one second to about one minute; periods that last for less than two minutes; periods that last for about five minutes; ten minutes; 15 minutes; 20 minutes; 30 minutes; 45 minutes; and times therebetween.

Our expectation is that the response of the cell, tissue, organ, or organism at the conclusion of a treatment period will be superior to the response expected if the chemical agent or physical stimulus had been delivered according to a different regimen (i.e., other than a regimen allowing delivery for about one second to about one hour and prohibiting delivery for about the next 1-6 hours).

While we refer to, for example, "treatment" and to chemical agents, therapeutic agents, neutraceuticals, and therapeutically beneficial signals, one of ordinary skill in the art will recognize that many of the therapeutic agents (e.g., organic compounds) and the other types of stimuli described herein can be administered prophylactically as well. Thus, the present compositions and methods are not limited in their application to diseased targets; they may also be applied to normal, healthy cells, tissues, organs and organisms. For example, to help maintain or improve the physiological state of a cell, tissue or organism, a stimulus can be applied as described herein to maintain or improve cell or tissue viability or function. Thus, the invention encompasses compositions and methods for prevention and treatment of a variety of diseases, disorders, metabolic syndromes, conditions, and the like, including tissue repair and rehabilitation following injury (e.g., intentional trauma or accidental trauma) as well as prevention of (e.g., an inhibition of the loss of muscle mass, bone density, and the like that occurs in the course of normal aging.

As discussed further below, the present compositions and methods can also be used to alter cell fate (e.g., the differentiation of stem cells) and therefore, alter the viability and function of a cell or tissue. Increasing the differentiation of stem cells within a tissue would increase the number of functional, differentiated cells within the tissue. At the level of an organism, the present compositions and methods can be assessed in terms of their prophylactic effect on health. For example, patients within a treated population may have a lower risk of developing a common condition such as cancer, autoimmune disease, heart disease, or a metabolic disorder (e.g., metabolic syndrome or diabetes). The effectiveness of prophylactic treatment may also be judged by better than expected physiological parameters, such as body mass index, bone density, muscle mass, blood pressure, blood glucose levels, and cholesterol levels. The outcome can be assessed relative to an untreated population or on a patient-by-patient basis comparing a given physiological parameter (or set of parameters) before and after treatment.

Accordingly, the invention features methods of influencing the fate of a cell by: providing a cell; exposing the cell to a high frequency, low magnitude physical stimulus, wherein the stimulus is applied to the cell for a first time for about one second to about one hour; allowing the cell to rest, free of the stimulus, for about the next 1-6 hours (e g, 1-3 hours), and exposing the cell to the stimulus for a second time for about one second to about one hour. The cell can be a stem cell (or the tissue, organ, or organism treated can include a stem cell). The stem cell can be a mesenchymal stem cell, a hematopoietic stem cell, a neural stem cell, or an adult stem cell. The cell can also be a partially differentiated cell. For example, the stem cell or the partially differentiated cell can be a precursor to an adipocyte, an osteocyte, a hepatocyte, chondrocyte, a neuron, a myocyte, a blood cell, an endothelia cell, an epithelial cell, or an endocrine cell.

As indicated above, the present compositions and methods can be applied prophylactically or therapeutically. For therapeutic application, a cell, tissue, organ, or organism may have been affected by a traumatic injury, including trauma induced intentionally (e.g., in the context of a surgical procedure). Alternatively, the cell, tissue, organ, or organism may be affected by a disease, disorder or condition for which a therapeutic agent is typically prescribed or a physical signal is thought to be beneficially applied. For example, a cell, tissue, organ, or organism may be affected by cancer, in which case the therapeutic agent can be a chemotherapeutic agent and the physical signal can be one generated in the context of radiation therapy. In other circumstances, a patient may have received a graft or tissue transplant, in which case the therapeutic agent can be an immunosuppressant. In other circumstances, the present methods apply where a patient would benefit from an increase in the number of cells (e.g., differentiating stem cells) within a given tissue and, ex vivo, where it is desirable to increase the proliferation of cells (e.g., stem cells) for scientific study, inclusion in devices bearing cells (e.g., polymer or hydrogel-based implants), and administration to patients. These examples are provided solely to illustrate particular embodiments of the invention.

In previous studies we found that inducing loads below those that typically arise even during walking affect the proliferation and differentiation of cells, including stem cells such as mesenchymal stem cells, as we as suppress adiposity, triglycerides, and free fatty acid production. In later studies, some of which are described below, we have further found that purposefully including defined periods of rest between a first and second load-inducing signal can result in an enhanced response to the second signal or to subsequent signals (e.g., a third or subsequent signal).

Thus, we describe herein compositions and methods for applying various stimuli (whether a prophylactic or therapeutic agent or a physical signal mediated by electricity, magnets, heat, light, x-rays or some other force or type of energy) to a cell, tissue, organ, or organism. In some embodiments, the stimuli are applied to enhance the viability and/or number of stem cells in a cell culture or in vivo. The methods can also be applied to direct the cells toward a certain path of differentiation. Where cellular viability and/or proliferation are improved (relative to what one would expect in the absence of treatment), the methods can be used to accelerate and augment the process of tissue repair and regeneration, help alleviate the complications of treatments (e.g., radio- and chemotherapy) which compromise cell viability, enhance the incorporation of tissue grafts, including allografts, xenografts and autografts, and inhibit the deleterious effects of aging.

The methods described herein can amplify and enhance the responsiveness and efficacy of cells, tissues organs, and organisms to a given chemical agent or physical stimulus through the use of a refractory or rest period, which we believe allows the cells, tissues, organs, or organisms to reset, perhaps to a more desirable state, before being administered another bout of the therapeutic stimulus or physical stimulus. While the invention is not limited to compositions and methods that achieve a desired outcome through any particular molecular mechanism, we believe the introduction of refractory or rest periods, as described herein, enables cells to recover sensitivity to chemical agents and physical stimuli.

We may also describe the outcome as an accelerated or augmented response to a given therapeutic stimulus or physical signal. As these methods can allow for a more effective response, follow-on advantages may include a reduction in dosage, thereby improving safety and reducing cost.

Accordingly, the invention features methods of treating a patient with a physiologically acceptable chemical (e.g., pharmaceutical) agent or physical stimulus, and the steps of the method include administering to the patient, or fitting the patient with, a device as described herein. Me device contains one or more chemical agents and/or delivers one or more physical stimuli to treat a condition with which the patient is suffering or to prevent (e.g., inhibit the severity of or delay the development of) undesirable condition. As the methods can be prophylactic or therapeutic, the patient may or may not have a damaged or defective organ or tissue. In some embodiments, the damaged or defective organ or tissue is an organ or tissue other than a damaged or defective bone or muscle tissue. In other embodiments, the cell, tissue, organ, or organism may be diseased, damaged or rendered defective by traumatic injury, a tissue damaging disease, neurodegenerative disease, aging, a congenital malformation, or a neural tube defect. For example, the invention encompasses methods of treating a patient for sarcopenia, osteopenia, or osteoporosis by administering to the patient a high frequency, low magnitude physical signal, wherein the signal is applied to the patient at least twice and each of the first and second applications lasts for about one second to about one hour, and wherein no signal is applied during an interval of about 1-6 hours between the first signal and the second signal, in this method or in the treatment or prevention of any other condition, the signal can be applied at least or about 2-4 times daily or the entire regimen of multiple stimulation with intervening rests can be repeated at least or about 2-4 times per day. For example, a patient may be subjected to periods of stimulation with intervening periods of rest, as described herein, for one to three hours, and that same 1-3 hour process can be repeated 2, 3, 4, 5, 6, or more times per day.

Any of the methods can include a step of identifying a cell, tissue, organ, or organism (e.g., a human or veterinary patient) in need of treatment (whether to maintain or improve health or to address a traumatic injury or disease condition). As noted, the methods are broadly applicable and can be used to modify the dosing regimen for many conventional treatments, including those for cancer (e.g., breast cancer, bone cancer, bladder cancer, a blood cancer (e.g., lymphoma or leukemia), brain cancer, cervical cancer, colorectal cancer, esophageal cancer, gastric cancer, lung cancer, renal cancer, skin cancer, pancreatic cancer, prostate cancer, or uterine cancer), heart disease, neurodegenerative disease (e.g., Alzheimer's disease, Parkinson's disease, or amyotrophic lateral sclerosis), psychiatric disorders (e.g., anxiety, bipolar disorder, depression, an eating disorder, an impulse control disorder, an obsessive compulsive disorder, schizophrenia, and Tourette's syndrome), an autoimmune disease (e.g., Addison's disease, Behcet's disease, Celiac disease, juvenile diabetes, Graves' disease, Lupus, Meniere's disease, psoriasis, restless legs syndrome, rheumatoid arthritis, and vasculitis), or a metabolic disorder (e.g., metabolic syndrome). For example, the methods of the invention can be used to maintain or improve symptoms of diabetes in a subject by providing to the subject a therapeutic stimuli (e.g., a physical signal), through repeated stimulation separated by a rest period of non stimulation sufficient to amplify the improvement of diabetes (e.g., by reducing or suppressing adipogenesis). In identifying a subject amenable to treatment, the methods can include a step of analyzing one or more of the genetic aberations associated with a condition (in this example, diabetes), of assessing basic physiological parameters (in this example, a subject's blood glucose levels), or by other methods known in the art (e.g., imaging techniques) for identifying a patient who is in need of treatment (in this example, a diabetic or pre-diabetic patient). Similarly for the prevention and treatment of obesity or a related medical condition, the present methods can safely be used as an intervention in pre-adolescents, adolescents (e.g. in the prevention and treatment of juvenile diabetes), and adults. Obesity-related medical conditions include cardiovascular disease, hypertension, osteoarthritis, rheumatoid arthritis, breast cancer, a cancer of the esophagus or gastrointestinal tract, endometrial cancer, renal cell cancer, carpal tunnel syndrome, chronic venous insufficiency, daytime sleepiness, deep vein thrombosis, end stage renal disease, gallbladder disease, gout, liver disease, pancreatitis, sleep apnea, a cerebrovascular accident, and urinary stress incontinence. These obesity-related medical conditions are amenable to treatment as described herein. While the methods of the invention are not limited to those that achieve a desired result by any particular cellular mechanism, it is our working hypothesis that application of a stimulus (e.g., a low magnitude, high frequency physical signal) to a tissue containing stem cells causes more of the stem cells to differentiate along a non-adipogenic path.

Accordingly, the methods of the invention can be used to suppress or reduce adipogenesis in a subject (e.g., a human or other mammal (e.g., a pet)) by providing to the subject a therapeutic stimulus (e.g., a physical signal) on a repeated basis separated by a refractory or rest period of little or no stimulation. The regime is such that the reduction or suppression of adipogenesis is greater than what would have been achieved with a more traditional treatment regime (e.g., a single daily treatment or administration of a stimulus every six, eight, or 12 hours). Subjects amenable to this treatment can include those diagnosed with being insulin resistant, overweight or obese, and at risk of being overweight or obese. The subjects can also be those diagnosed as having diabetes or metabolic syndrome.

Unlike many conventional methods that strive to maintain a constant application of a stimulus to a cell, tissue, organ, or organism, the present methods require intervening rest periods, with the goal of providing the cell, tissue, organ, or organism with periods in which it is exposed to little or no stimulus. Depending on the source of the stimulus, the transition from the period of application to the period or rest may be abrupt or more gradual. For example, if the source of the stimulus is a physical device (e.g., an ultrasound or x-ray machine), the transition between the end of the period of stimulus application and the beginning of the rest period will occur very quickly—as quickly as the machine is able to move from an "on" to an "off" position and halt the projected sounds waves or x-rays. In other instances, such as the release of a compound from a controlled release formulation that delivers bursts of the contained compound, the transition may take longer. Thus, a wave representing the alternating pattern of stimulus delivery and rest include square waves or, in other embodiments, undulating or tri-angle-like waves (as illustrated in FIG. 1). Any of the methods described herein can be carried out using a variety of stimulus patterns. For example, a chemical agent or physical stimuli can first be administered in an abrupt pattern (e.g., as represented by a square wave) and subsequently, following the rest period, in another patter (e.g., in a manner represented by a sine or sawtooth wave or as a chirp or random/chaotic wave).

The methods of the invention can be used to enhance or increase proliferation (as assessed by, e.g., the rate of cell division), of a cell and/or population of cells in culture. The cultured population may or may not be purified (i.e., mixed cell types may be present, as may cells at various stages of differentiation). Numerous cell types are encompassed by the methods of the invention, including bacterial cells, yeast cells, or other mammalian cells (including, e.g., explants or organs), and adult stem cells (regardless of their tissue source), embryonic stem cells, stem cells obtained from, for example, the umbilical cord or umbilical cord blood, primary cell cultures and established cell lines. Useful cell types can include any form of stem cell. Generally, stem cells are undifferentiated cells that have the ability both to go through numerous cycles of cell-division while maintaining an undifferentiated state and, under appropriate therapeutic stimuli, to give rise to more specialized cells. In addition, the present methods can be applied to stem cells that have at least partially differentiated (i.e., cells that express markers found in precursor and mature or terminally differentiated cells).

The methods described here can be carried out by providing, to a target (whether it be a cell, tissue, organ, or organism), a therapeutic stimuli, such as a physical signal, according to a stimulate-rest-stimulate protocol. The therapeutic stimuli can be administered other than by a physical force. Forces that can be applied according to the methods described herein include an ultrasound signal (e.g., an ultrasound signal that generates about the same tissue displacement as the high frequency, low magnitude physical forces described herein). The ultrasound signal can be, for example, about 2.5 watts. Other forces include electrical force (e.g., a current), magnetic force (e.g., the application or production of a magnetic field), heat energy, light energy (e.g., an infra-red, ultraviolet, or visible light), sound energy ultrasound), and the force of x-rays. As noted, a stimulus, regardless of its type or source, is supplied repeatedly, with a period of application or administration followed by a refractory or rest period of little or no stimulation. As noted, the stimulus can be administered two, three, or four times with one, two or three periods of rest, respectively. The duration of the rest periods will typically range from about one to about three hours. The entire regime, with the stimulus and rest periods as described herein, can be repeated periodically (e.g., daily or weekly).

The compositions and methods of the invention can be described as producing an amplified response. For example, the response achieved may be one that is simply larger or more robust than the response that would have been produced by applying the stimulus differently. For example, cellular differentiation that leads to increased bone density or increased muscle mass may be more robust when the physical signal driving the differentiation is delivered in two or three bouts, as described herein, rather than all at once (e.g., once daily). However, as the present compositions and methods can be used to maintain the viability or function of a cell, tissue, organ, or organism, the response may also be described as amplified when it inhibits or slows the decline one would have expected to see if the stimulus had been administered differently (e.g., if a second stimulus had been applied without the required rest period). In other words, the present compositions and methods can result in an improvement or in an inhibition of a worsening of a population of cells (e.g., as occurs with age).

Any of the devices that deliver the types of signals described above can be modified to include a timer or a similar component that will deliver the signal in accordance with the timing described herein. The devices can also be programmed so that a user can select any one of a given number of delivery schedules. For example, a device can be programmed so the user can select a delivery period of about two seconds to about 20 minutes and, independently, a rest period of about one hour to about three hours. As noted, the stimulus can be delivered two, three, four, or more times. Below, we discuss the administration of low magnitude, high frequency stimuli, and devices can be programmed to deliver such a signal (e.g., a burst of about 0.5 s of a 40 Hz, 0.3 g vibration at least or about every second during the treatment period). While the invention is not so limited, it is most likely that the devices that will be programmed as described here will be implanted devices (e.g., an orthopedic device with electric circuitry or magnets to aid healing) or a device that is otherwise constantly associated with a patient (e.g., a cast, brace, bandage, wheelchair, or the like). Devices for use ex vivo, for example in delivering a stimulus as described herein to cultured cells, can be incorporated into tissue culture ware, such as plates, flasks, rotating platforms, and incubators.

While prior studies have demonstrated the importance of cell or substrate distortion in orchestrating a cellular reaction, recent in vivo evidence suggests that some cell responses to physical signals em occur in the absence of matrix strain, through acceleration rather than loading of the tissue. See Judex (*J Musculoskelet Neuronal Interact* 10:3-11 (1987)). The physical acceleration of a cell may thus represent a generic signal that can transmit physical challenges altering intracellular cytoskeletal or cell:matrix inter-relationships, rather than requiring transmission of the physical information through the deviation of the substrate, per se.

The therapeutic stimuli, if introduced as physical signals (e.g., vibrations), can have a magnitude of at least or about 0.01-10.0 g. For the sake of added clarity, all values within this range are included. Thus, stimuli useful in the present invention include 0.015, 0.02, 0.025, 0.03, 0.035 g and so on. Signals of low magnitude are expected to be effective. Accordingly, the methods described herein can be carried out by applying at least or about 0.1-1.0 g (e.g., 0.2-0.6 g, inclusive (e.g., 0.2 g, 0.3 g, 0.4 g or 0.6 g and values therebetween)) to a cell, tissue, organ, or organism. The frequency of the physical signal can be at least or about 5-1,000 Hz. For the sake of added clarity, all values within this range are included. For example, the frequency of a physical signal delivered in the context of the present invention can be, e.g., at least or about 15 or 20-200 Hz, inclusive (e.g., 30-90 Hz (e.g., 30, 35, 40, 45, 50, 55 or 90 Hz)). For example, the frequency of the physical signal can be about 5-100 Hz, inclusive (e.g., about 40-90 Hz (e.g., 50, 60, 70, 80, or 90 Hz) or 20-50 Hz (e.g., about 20, 25, 30, 35 or 40 Hz), a combination of frequencies (e.g., a "chirp" signal from 20-50 Hz), as well as a pulse-burst of physical information (e.g., a 0.5 s burst of 40 Hz, 0.3 g vibration given at least or about every 1 second during the treatment period). The therapeutic stimuli can last at least or about one second to about one hour, inclusive (e.g., 2, 5, 10, 15, 20, 30, 45, or 60 minutes). The physical signals can be provided at least twice daily separated by at least about one hour to about three hours of prohibited release.

Low-magnitude, high-frequency physical signals can be provided by placing the cell, tissue, organ, or organism on a device with a vibrating platform. An example of a device that can be used is the JUVENT 1000 (by Juvent, Inc., Somerset, N.J.) (see also U.S. Pat. No. 5,273,028). The source of the physical signal (e.g., a platform with a transducer, e.g., an actuator, and source of an input signal, e.g., electrical signal) can be variously housed or situated (e.g., under or within a chair, bed, exercise equipment, mat (e.g., a mat used to exercise (e.g., a yoga mat)), hand-held or portable device, a standing frame or the like). The source of the physical signal (e.g., a platform with a transducer, e.g., an actuator and a source of an input signal, e.g., electrical signal) can also be within or beneath a floor or other area where people tend to stand (e.g., a floor in front of a sink, stove, window, cashier's desk, or art installation or on a platform for public transportation) or sit (e.g., a seat in a vehicle (e.g., a car, train bus, or plane) or wheelchair). The sigma an also be introduced through oscillatory acceleration in the absence of weightbearing (e.g., oscillation of a limb), using the same frequencies and accelerations as described above.

Electromagnetic field signals can be generated via Helmholtz coils, in the same frequency range as described above, and within the intensity range of 0.1 to 1000 micro-Volts per centimeter squared (inclusive). Ultrasound signals can be generated via piezoelectric transducers, with a carrier wave in the frequency range described herein, and within the intensity range of about (1.5 to 500 milli-Watts per centimeter squared (inclusive). Ultrasound can also be used to generate vibrations as described herein.

The transmissibility (or translation) of signals through the body is high. Therefore, signals originating at the source, e.g., a platform with a transducer and a source of, e.g., an electrical signal, can reach various parts of the body that may not be in contact with the platform. For example, it the subject stands on the source of the signal, e.g., the platform described herein, the signal can be transmitted through the subject's feet and into upper parts of the body, e.g., abdomen, shoulders, neck, arms, etc.

While we tend to use the term "organism" we may also use the terms "subject", "patient", "mammal", and "human". Subjects, patients, mammals, and humans are all organisms and can be treated according to the methods described herein for organisms.

The stimuli delivered to an organism can be, for example, vibrations, magnetic fields, electrical currents and ultrasound. These types of stimuli can be readily generated with appropriate means that are well known in the art. For example, vibrations can be generated by transducer(s) (e.g., actuator(s), electromagnetic actuator(s)), magnetic field can be generated with Helmholtz coil(s), and ultrasound can be generated with piezoelectric transducer(s).

As noted above, the stimuli can be delivered using a device that is wholly confined within the subject (e.g., an implantable device). However, the stimulus can also be delivered via an ingestible tablet or capsule, dual-phase or tri-phase drug release systems (such as those described in U.S. Pat. No. 7,790,150), an implantable pump (such as the pump described in U.S. Pat. Nos. 7,813,809 and 7,813,802), a opthalmic/contact lens (as described, for example, in U.S. Pat. No. 7,811,601), an orthopedic device, a dental implant, or a pacemaker. Such a device can be configured by one of skill in the art to deliver the therapeutically beneficial signal to a cell, tissue, organ, or organism or to deliver a therapeutic agent (e.g., pharmaceuticals like large and small molecules, antibodies, antivirals (including agents targeted to HIV, HPV, and influenza viruses), chemotherapeutics, anti-cancer substances, radionuclides, vitamins, antibiotics, immunosuppressants, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/ or antithrombotic agents, local anesthetics, ophthalmics, prostaglandins, anti-depressants, anti-psychotic substances, anti-emetics, imaging agents). Drug delivery, for example, could be provided by liposomes or other time release methods that can be pulsed (e.g., by chemical structure or enabled by transcutaneous signaling, as described in U.S. Pat. Nos. 7,813,802 and 7,813,809) to build in a refractory or rest period. This delivery would be carried out by regulating the release of the therapeutic agent or therapeutically beneficial signal for about one second to about one hour (e.g., for less than two minutes), by the use of a simple timer or the like, followed by a refractory or rest period that prohibits release of the therapeutic agent or signal for at least about one to about three hours. The device would regulate the release and non-release periods on a regularly or irregularly repeating cycle. The given refractory period of non-release can be scheduled such that the response of the subject to the second release of the therapeutic agent or therapeutically beneficial signal is greater than the response to the initial release. A subject can be fined with such a device for the treatment of damaged or defective organs, or for the treatment of tissues other than a damaged or defective bone or muscle tissue. Such damaged or defective organs can include those damaged or rendered defective by traumatic injury, a tissue damaging disease, neurodegenerative disease, a congenital malformation or medical procedure, or a neural tube defect and can be treated through the use of compositions such as found in U.S. Pat. No. 7,786,074.

Any given therapeutic stimulus and regimen can be changed and regulated based on the condition, infirmity or disease. For example, as the metabolism in a younger subject may be more responsive, a shorter refractory or rest period may be used than for an older or more ill subject (e.g., cancer treatment by radiation therapy). The ability to regulate the invention in this way would allow the maximization of the biologic response (e.g., the augmentation of repair) by optimizing the refractory period and the time of application of the therapeutic stimulus or physical signal for a given subject.

Therefore, the therapeutic stimuli can be delivered in a variety of ways, including by physical means by way of Whole Body Vibration through a ground-based vibrating platform or weight-bearing support of any type. In the case of cells in culture, the culture dish can be placed directly on the platform or vibration source (e.g. a loudspeaker). Optionally, the platform can be incorporated within a cell culture incubator or fermentor so that the signals can be delivered to the cells while maintaining the temperature and pH of the cell culture medium. For a whole organism, the platform can contact the subject directly (e.g., through bare feet) or indirectly (e.g., through padding, bedding, shoes, or clothing as appropriate). The platform can essentially stand alone, and the subject can come in contact with it as they would with a bathroom scale (i.e. by simply stepping and standing on an upper surface). The subject can also be positioned on the platform in a variety of other ways. For example, the subject can sit, kneel, or lie on the platform. The platform may bear all of the patient's weight, and the signal can be directed in one or several directions. For example, a patient can stand on a platform vibrating vertically so that the signal is applied in parallel to the long axis of for example, the patient's tibia, fibula, and femur. In other configurations, a patient can lie down on a platform vibrating vertically or horizontally. A platform that oscillates in several distinct directions could apply the signal multi-axially, e.g., in a non-longitudinal manner around two or more axes. Devices can also deliver the signal focally, using local vibration modalities (e.g., to the subject's abdomen, thighs, or back), as well as be incorporated into other devices, such as exercise devices. The therapeutic stimuli can also be delivered by the use of acceleration, allowing a limb, for example, to oscillate back and forth without the need for direct load application, thus simplifying the constraints of local application modalities (e.g., reducing the build-up of fat in limb musculature following joint replacement).

Independent of the magnitude of the regimen, our work indicates that a therapeutic stimuli's ability to influence MSC (mesenchymal stem cell) lineage allocation can be markedly enhanced if the stimulus is separated into two brief applications separated by a refractory or rest period of at least one hour. This indicates that the scheduling of events (the treatment regimen) is at least as important as the overall duration of the challenge. However, under extreme adipogenic constraints, only the high magnitude strain regimen as effective in countermanding adipogenesis, suggesting that there is an identifiable and critical combination of therapeutic stimulus parameters to combat deleterious environmental cues. As described in the examples below, applying the LIV signal three times daily, while adhering to a three hour rest period between the application of the stimulus, markedly increased the ability of the physical challenge to inhibit fat formation.

Our working hypothesis is that essentially all responses by cells, tissues, and organisms to a therapeutic stimuli or physical signal can be amplified and enhanced through the use of a rest or refractory period that allows the cells, tissues, and organisms to reset, perhaps at a higher level, before being administered another bout of therapeutic stimuli. For example, two twenty-minute sessions of either low intensity vibration or high magnitude strain suppressed adipogenesis when a one hour refractory period was provided between sessions. The ability of therapeutic stimuli to inhibit adipogenesis further increased with multiple loading sessions as long as a refractory period was incorporated. The data discussed in the Examples below indicate that therapeutic stimuli can directly bias mesenchymal stem cell lineage selection toward higher order connective tissues, the degree to which they are capable of doing so is more dependent on event scheduling than load magnitude or duration. In other words, we believe the presence of a biological refractory period is independent of the type of therapeutic stimuli. A full day of rest between sessions is not required to "reset" the responsiveness of a cell, tissue, organ, or organism, meaning that the impact of therapeutic stimuli or physical signals on defining the response may be accentuated by incorporating several brief sessions within any given twenty-four hour period. These brief but repetitive loading challenges can accrue an adaptive response in a fashion much greater than that achieved in a single daily session. Therefore, the scheduling of therapeutic agents or therapeutically beneficial signals may be as important as the stimuli of signals themselves. As such multiple daily sessions of therapeutic stimuli or physical signals could be leveraged in cases of rehabilitation and recreation, particularly in the context of combating a disease like childhood obesity or the degradation of the musculoskeletal system that parallels aging or functional compromise.

With the loading systems described herein, it becomes possible to compare biologic responsiveness to the spectral extremes of therapeutic agents and therapeutically beneficial signals and, through controlled changes in the schedule of the loading regimen, to hone in on optimized parameters of an influential loading regimen.

In another aspect, the present invention features methods for determining a sufficient refractory period to produce an increased or desirable effect on a cell, tissue, organ, or organism. These methods can be carried out by providing an assay that includes a cell, tissue, organ, or organism. For example, the assay can be one that tests cellular proliferation or differentiation (e.g., by the expression of phenotypic markers). In the method, one can then stimulate the cell, tissue, organ, or organism twice, for a time sufficient to provide a desired effect on the cell, and separate the two stimuli by a refractory or rest period with no stimulus to allow the cell to reset. These steps are repeated with rest periods and/or stimulation periods of varying length and/or intensity and the parameter being assayed (e.g., cellular proliferation) is then assessed. In this manner, one can determine the treatment regime(s) that produce an increase in the desired effect on the cell, tissue, organ, or organism.

EXAMPLES

Example 1: Materials and Methods

Mesenchymal stem cells (MSC) grown under media conditions that promote adipogenesis by 5-8 days were exposed to two distinct physical regimens. High magnitude stray (HMS) and low intensity vibration (LIV) were delivered, beginning with a once daily, long duration (6 hours) HMS protocol known to prevent adipogenesis. To determine if modifications in delivery of the HMS and LIV regimens could influence efficacy, the duration (from 20 min/day) and number (1-3 times per day) of daily applications were altered, delivered in a manner to determine if a refractory period altered the biologic response (events separated by about 1-6 hours). Molecular pathways involved in translating physical effects into a cellular response were compared between HMS and LINT challenges to determine if similar signal transduction pathways were utilized in responding to these distinct physical stimuli.

Reagents used include fetal bovine serum from Atlanta Biological (Atlanta, Ga.); culture media, trypsin-EDTA reagent, antibiotics, Lipofectamine 2000, reverse transcriptase, Taq polymerase and siRNA from Invitrogen; insulin and SB415286 from Sigma-Aldrich; DKK-1 from R & D Systems (Minneapolis, Minn.); and RNA isolation it from Qiagen (Valencia, Calif.).

C3H10T1/2 embryonic mesenchymal stem cells were maintained in growth medium (α-MEM, 10% FBS, 100 μg/ml penicillin/streptomycin). Cells were plated at a density of 6,000-10,000 cells per $cm^2$ in collagen-1 coated silicone membrane plates and cultured for two days before loading protocols began. Adipogenic medium included 0.1 μM dexamethasone, 5 μg/ml insulin, and in some cases, 50 μM indomethacin. If noted, MSC were transfected with siRNA (100 nm) in serum-free OptiMEM overnight before replacing the medium. Multi-potential medium contained 50 μg/ml ascorbic acid, 1 μM β-glycerophosphate, 10 nM dexamethasone, 10 nM all trans-retinoic acid, 5 μg/ml insulin, 0.5 mM 3-isobutyl-1-methylxanthine (IBMX).

Key experiments were replicated in a marrow derived mesenchymal stem cell line (mdMSC) generated from C56/BL6 wild-type mice using the procedure of A. Peister, et al. (*Blood* 103:1662-1668 (2004)). These cells readily undergo differentiation into osteogenic, adipogenic or alternative lineages using standard modifiers.

High Magnitude Strain (HMS):

Uniform biaxial strain was applied to C3H10T1/2 cells or mdMSC plated on collagen-1 coated silicone membrane plates using a biaxial deformation device. Application of the loading regimen consisted of peak strains of 2% at 10 cycles/minute for times specified (ranging from 20 min/day to 6 hours/day). All cultures remained in the incubator during these protocols.

Low Intensity Vibration (LIV):

To deliver LIV to cultured MSC, an amplified loudspeaker generated controlled 90 Hz 0.6 g (where 1.0 g is Earth's gravitational field, or 9.8 $m/s^2$) standing wave accelerations/decelerations through the wells of culture dishes. Dishes were removed from the incubator during the loading periods (up to three times per day) and set on the lab-bench (control) or, for LIV, on the loudspeaker.

Nuclear and Cytoplasmic Protein Fractionation:

The cells were washed with 1× phosphate-buffered saline, the cell pellet was re-suspended in 0.33 M sucrose, 10 mM Hepes, pH 7.4, 1 mM $MgCl^2$, 0.1% Triton X-100 (pellet versus buffer, 1:5) and placed on ice for 15 minutes. After centrifugation at 3,000 rpm for 5 minutes, the supernatant was collected (cytoplasmic fraction). The pellet was re-suspended in 0.45 M NaCl and 10 mM Hepes, pH 7.4, and placed on ice for 15 minutes. After centrifugation at 12,000 rpm for 5 minutes, the nuclear fraction supernatant was collected.

Real-Time RT-PCR:

Total RNA was isolated by using the RNeasy Plus Mini kit (Qiagen). Reverse transcription was performed with 1 µg of RNA in a total volume of 20 µl per reaction. Real time PCR was performed on a BioRad iCycler (Hercules, Calif.). 25 µl amplification reactions contained primers at 0.5 µM, dNTPs (0.2 mM each) in PCR buffer and 0.03 U Taq polymerase along with SYBR-green (Molecular Probes, Eugene, Oreg.) at 1:150,000. Aliquots of cDNA were diluted 5-5000 fold to generate relative standard curves to which sample cDNA was compared. PTHR1, OC and 18S primers are below: PTHR1 forward, 5'-CAAGAAGTGGATCATC-CAGG-3' (SEQ ID NO 1), PTHR1 revere, 5'-TAGTGGA-CACCGAAGAGIGG-3' (SEQ ID NO 2), OC forward, 5'-CTGACCTCACAGATGCCAA-3' (SEQ ID NO:3); OC reverse, 5'-GGTCTGATAGCTCGTCACAA-3 (SEQ ID NO:4); 18S forward, 5'-GAACGTCTGCCCTATCAACT-3) (SEQ ID NO:5); 18S reverse, 5'-CCAAGATCCAACTAC-GAGCT-3' (SEQ ID NO:6). Standards and samples were run in triplicate. PCR products from all species were normalized for the amount of 18S amplicons in the RT sample, which was standardized on a dilution curve.

Western Blotting:

Details were as in Sen, et al. (*Endocrinology* 149:6065-6075 (2008)). Antibodies included those directed against active β-catenin (Upstate, Temecula, Calif.), total β-catenin (BD, Bedford, Mass.), total-GSK3β (Chemicon, Billerica, Mass.), aP2, PPARγ, adiponectin COX2, NFATc1 and tubulin (Santa Cruz, Calif.). Densitometry was determined using NIH ImageJ, 1.37v.

Histochemical Staining:

After fixation in 2% formaldehyde, cells were rinsed before staining for cytoplasmic triglyceride droplets with oil-red-O.

Statistical Analysis:

Results are expressed as the mean±SEM. Statistical significance was evaluated by two-way ANOVA or t-Test (GraphPad Prism). Densitometry data where given, were compiled at least three separate experiments in a series.

Example 2: Suppression of Adipogenesis by High and Low Magnitude Physical Signals Both two and six hours of continuous HMS, at 10 cycles per minute (0.17 Hz; totaling 1200 or 3600 cycles of strain, respectively) prevented acquisition of the fat phenotype over seven days. Two hours per day HMS repressed the fat marker adiponectin by more than half that of control in cultures, while adiponectin protein expression was completely inhibited by 6 hours daily HMS. Reducing HMS duration to 40 mm/day was still effective, while 20 mm/day was not. In contrast, when the HMS regimen was bisected into two 20 minute periods each day, with loading events separated by at least 1 hour, fat formation was almost entirely inhibited to a degree similar to that seen with 6 hours of daily loading. This effect was also evident examining the fat transcription factor, PPARγ, which was decreased more significantly when a 40 minute daily regimen was divided into two separate 20 minute sessions. That these twice daily 20 minute treatments of HMS were more effective than either single doses of 40 or 120 minutes of HMS exposure indicated that a refractory period inserted between physical treatments enhanced a biologic system's ability to respond to physical challenges.

Instrumentation for the LIV signal provided dosing for 20 minutes per treatment. Daily treatments of either 20 or 40 minutes of LIV for seven days failed to suppress adipogenesis. Similar to that observed with HMS, however, when the LIV regimen was divided into two daily 20 minute applications, adiponectin and PPARγ were decreased, with a concurrent reduction in the fat marker aP2 and the development of lipid granules. While HMS is known to increase cytoplasmic β-catenin, LIV treatment, even when suppressing adipogenesis, did not.

The addition of indomethacin to adipogenic media accelerated the rate of adipogenesis from 7-8 days to 4-5 days. When cultures were grown in the highly adipogenic media and assayed at day four, twice daily LIV failed to inhibit adipogenesis, while HMS was efficacious, causing decreases in adiponectin, PPARγ and increasing active and total β-catenin.

Example 3: Suppression of Adipogenesis is Dependent on the Refractory Period Between Loading Events The ability of both HMS and LIV to suppress adipogenesis in MSC was enhanced by incorporating a refractory period between loading events. To further define the specifics of the refractory period, MSC were subject to two LIV treatments each day over the course of seven days, with physical application separated by either 1 or 3 hours. Separation of two LIV treatments by 1 hour was effective in reducing adiponectin by 30%±8%, p<0.05, as shown by densitometry of adiponectin bands in a series of three experiments. The physical suppression was significantly more effective when LIV treatments were separated by a 3 hour rest period, reducing adiponectin levels in this series of three experiments by 70%±5% (p<0.01). Increasing the refractory period from 3 hours to 6 hours failed to further influence efficacy.

The role of a refractory period in the physical suppression of adipogenesis was further examined by increasing the number of 20 minute LIV treatments from two to three each day, increasing the number of LIV treatments from two to three bouts daily, each bout separated by 3 hours, significantly enhanced the ability of these physical signals to inhibit adipogenesis. The refractory period of 3 hours in this experiment allowed for the completion of three bouts of stimulus in 10 hours. Densitometry on a series of three experiments shows that twice daily LIV spaced by 3 hours reduced adiponectin by 40%±6% compared to control, p<0.05, while three treatments per day reduced adiponectin protein by 70%±2% (P<0.01 compared to control).

The efficacy of LIV to inhibit adipogenesis was also studied in marrow derived mesenchymal stem cells (mdMSC), where adipogenesis required eight days for formation of measurable adiponectin and lipid granules in control cultures. Separation of two LIV treatments by 1 hour each day for eight days was ineffective in reducing adiponectin, but with separation of loading events increased to 3 hours, LIV repressed adiponectin, an attribute further enhanced with three treatments daily each separated by 3 hours. LIV, therefore, was able to significantly and robustly reduce acquisition of fat phenotype when a second 20 minute LIV treatment was added each day. The second treatment achieved efficacy only if it was delivered after a rest period of at least 1 hour between physical treatments. The ability of the second LIV treatment to suppress adipogenesis was enhanced by increasing the rest period to at least 3 hours.

Example 4: Physical Signals Enhance MSC Responsiveness to BMP2

To evaluate whether physical signals promote MSC entry into the osteogenic lineage, C3H10T1/2 MSC were grown in a multi-potential medium for eight days, which supports both adipogenic and osteogenic differentiation, and treated twice daily with LIV separated by 3 hours. LIV treated cultures showed a 33%±15% (p<0.001) enhancement of PTHR1 expression. LIV alone, however, failed to significantly increase the osteogenic phenotype as measured by osterix and osteocalcin mRNA expression.

To query whether physical signals preserved MSC differentiation potential, C3HT101/2 MSC were cultured in adipogenic medium for seven days, with or without twice daily LIV separated by greater than 3 hours, before switching to a multi-potential medium that included 100 ng/ml of BMP2. Treatment with LIV in the absence of BMP2 failed to significantly induce either PTHR1 or osteocalcin mRNA. In contrast, BMP2 treatment increased both markers of osteoblast phenotype in control and LIV treated cultures, even after seven days in the adipogenic medium. Importantly, treatment during the adipogenic culture with twice daily LIV significantly enhanced this BMP2 response, as shown by a 100%±26% (p<0.01) increase above control culture in PTHR1, and an increase of 50%±6% in osteocalcin (p<0.05).

Example 51: Inhibition of Adipogenesis by LIV Requires β-catenin Signaling Via GSK30 Inhibition HMS is known to prevent adipogenesis by inhibiting GSK3β, which results in preservation and activation of β-catenin. In contrast to the β-catenin activation measured with HMS, the anti-adipogenic impact of the LIV treatment regimen did not achieve this by increasing levels of β-catenin in the whole cell lysates. However, by fractionating nuclear and cytoplasmic proteins, LIV was shown to have a weak effect to increase nuclear active β-catenin. It was then determined if β-catenin was required for LIV efficacy. siRNA targeting β-catenin (+siCat) or a siRNA scrambled control (−siCat) was added to MSC as previously described. When β-catenin was knocked down, the ability of LIV to inhibit adipogenesis was essentially abrogated, as shown by near equivalency of adiponectin and PPARγ immunoblots in the control and LIV treated cultures. The prevention of adipogenesis by SB415286, a GSK3β inhibitor, was also blocked by targeting β-catenin in these conditions, showing that declines in β-catenin are permissive to adipogenesis. These data provide additional support for a mechanism by which physical signals prevent adipogenesis through the inhibition of GSK3β with subsequent protection and activation of β-catenin.

It was considered whether LIV's potential conscription of GSK3β/β-catenin pathway might be achieved via an autocrine loop requiring Wnt signaling, DKK1 was added to cultures at doses known to inhibit Wnt binding Lrp receptors, but failed to block LIV's ability to inhibit adipogenesis. Together, these data suggest that the LIV signal requires access to β-catenin, does not require paracrine Wnt binding, and invokes GSK3β inhibition.

Physical signal inhibition of GSK30 also allows the nuclear accumulation of NFATc1, a transcription factor responsible for increased COX2 expression in MSCs. It was next determined whether LIV induced inhibition of GSK30 as potent enough to modulate NFATc1/COX2 signaling. In MSC treated with LIV (two 20-minute sessions/day separated by 3 hours). Western blot failed to show a consistent increase in COX2 expression in whole lysates. However, by fractionating nuclear and cytoplasmic proteins, LIV was shown to increase both NFATc1 nuclear accumulation and COX2 expression. This was also true when LIV was delivered to mdMSC: NFATc1 was increased in the nuclear fraction and COX2 rose in the cytoplasm. To illustration the differential effect of GSK3β inhibition on β-catenin and NFATc1 activation in mdMSCs, GSK3β was inhibited by the small molecule SB415286; it was clear that while β-catenin was activated with a dose of SB415286 at 5 μM, an effect on COX2 was not seen until a dose of 10 μM, an effect preceded by nuclear accumulation of NFATc1.

To determine the degree of GSK313 involvement in the enhancement of NFATc1/COX2 signaling by LIV, GSK3β was knocked down by targeted siRNA. When GSK3β was deficient, nuclear NFATc1 increased, as did COX2. However, the weak LIV induction of COX2 was ablated when GSK3β protein was deficient, shown by an absence of further increase in COX2 in MSC where GSK3β was silenced. This confirmed that alterations in nuclear NFATc1 caused by physical signals required the presence of GSK3β.

A number of embodiments of the invention have been described. Nevertheless, it will be understood that various modifications may be made without departing from the spirit and scope of the invention. Accordingly, other embodiments are within the scope of the following claims.

What is claimed is:

1. A method of enhancing a cell response to a high frequency, low magnitude physical stimulus, the method comprising:
   providing a cultured cell;
   providing a device configured to deliver the high frequency, low magnitude physical stimulus toward the cultured cell;
   exposing the cultured cell to the physical stimulus, wherein the physical stimulus is applied to the cultured cell for a first session comprising about one second to about one hour;
   providing for a refractory period wherein the same cultured cell is free of the physical stimulus for about the next 1-3 hours; and
   exposing the same cultured cell to the physical stimulus for a second session comprising about one second to about one hour immediately after the about 1-3 hours of being free of the physical stimulus,
   wherein the response is enhanced relative to a cultured cell receiving the same stimulus without the refractory period, and wherein the cultured cell is a purified tissue culture.

2. The method of claim 1, wherein the cultured cell comprises a mammalian cell.

3. The method of claim 1, wherein the physical stimulus is delivered by vibration.

4. The method of claim 1, wherein the frequency is about 5-1,000 Hz and wherein the magnitude is about 0.01-10.0 g.

5. The method of claim 1, further comprising providing the cultured cell in the device, wherein the device is a cell culture incubator.

6. The method of claim 1, wherein a response by the cultured cell to the physical stimulus is an increase in cellular proliferation.

7. The method of claim 1, wherein the device is configured to deliver the high frequency, low magnitude, physical stimulus toward the cultured cell when the cultured cell is disposed in an in vitro growth medium.

8. The method of claim 1, wherein the cultured cell is disposed in an in vitro growth medium.

9. The method of claim 1, wherein the cultured cell is in tissue culture.

10. The method of claim 1, wherein the time period of the physical stimulus are selected from the group consisting of about 2, 5, 10, 15, 20, 30, 45 or 60 minutes.

11. The method of claim 1, wherein the frequency of the physical stimulus is about 15 to about 200 Hz.

12. The method of claim 1, wherein the frequency of the physical stimulus is about 5 to about 100 Hz.

13. The method of claim 1, wherein the magnitude of the physical stimulus is about 0.1 to 1.0 g.

* * * * *

UNITED STATES PATENT AND TRADEMARK OFFICE
CERTIFICATE OF CORRECTION

| | | |
|---|---|---|
| PATENT NO. | : 10,029,089 B2 | Page 1 of 1 |
| APPLICATION NO. | : 13/879551 | |
| DATED | : July 24, 2018 | |
| INVENTOR(S) | : Clinton Rubin et al. | |

It is certified that error appears in the above-identified patent and that said Letters Patent is hereby corrected as shown below:

In the Specification

Column 1, Line 18:
"This invention was made with government support awarded by the National Institutes of Health under Grant No. AR43498. The U.S. government has certain rights in this invention."
Should read:
-- This invention was made with government support under Grant Numbers AR043498, AR042360 and AR056655 awarded by the National Institutes of Health. The government has certain rights in the invention. --

Signed and Sealed this
Twenty-second Day of January, 2019

Andrei Iancu
*Director of the United States Patent and Trademark Office*

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caagaagtgg atcatccagg                                                20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic

```
                         primer

<400> SEQUENCE: 2
tagtggacac cgaagagtgg                                               20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctgacctcac agatgccaa                                                19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtctgatag ctcgtcacaa                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaacgtctgc cctatcaact                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccaagatcca actacgagct                                               20
```